United States Patent [19]
Weidenbenner

[11] Patent Number: 6,051,011
[45] Date of Patent: Apr. 18, 2000

[54] SURGICAL HANDPIECE

[75] Inventor: John Joseph Weidenbenner, Ballwin, Mo.

[73] Assignee: Bausch & Lomb Surgical, Inc., Claremont, Calif.

[21] Appl. No.: 08/919,735

[22] Filed: Aug. 28, 1997

[51] Int. Cl.[7] .................................................. A61B 17/32
[52] U.S. Cl. .......................................... 606/171; 606/174
[58] Field of Search ................................ 606/1, 170, 171, 606/174, 177, 167, 51, 52; 335/87, 240, 251, 258, 260; 30/208, 209, 210, 272.1

[56] References Cited

U.S. PATENT DOCUMENTS

| | | | |
|---|---|---|---|
| 3,832,776 | 9/1974 | Sawyer | 30/272 |
| 3,899,829 | 8/1975 | Storm et al. | 30/228 |
| 4,200,106 | 4/1980 | Douvas et al. | 128/305 |
| 4,210,146 | 7/1980 | Banko | 128/305 |
| 4,258,716 | 3/1981 | Sutherland | 128/318 |
| 4,428,748 | 1/1984 | Peyman et al. | 604/22 |
| 4,433,687 | 2/1984 | Burke et al. | 128/318 |
| 4,590,936 | 5/1986 | Straub et al. | 128/305 |
| 4,622,503 | 11/1986 | Sundblom et al. | 318/645 |

(List continued on next page.)

FOREIGN PATENT DOCUMENTS 835436  6/1981  U.S.S.R. .

OTHER PUBLICATIONS

Grieshaber & Co. Inc., Sutherland Rotatable Intraocular Microscissors Catalog.
Grieshaber, The Grieshaber Sterilization Case and Silicone Insert Catalog.
Membrane Peeler Cutter Automated Vitreous Scissors and Hooked Needle—Arch Ophthalmol—vol. 99, Jan. 1981, pp. 152–153.
MPC Membrane Peeler Cutter, Automated Microscissors and Pic, Ophthalmic Surgical Instruments.
The Proportiona Control System for Sutherland Intraocular Scissors and Forceps—Ophthalamic Surgical Instruments.
Grieshaber—MPC The Membrane Peeler Cutter—Automated Microscissors and Hooked Needle.
Sutherland Rotable Intraocular Microscissors, Grieshaber & Co. Catalog.
The Smooth Removers, Storz Instrument company Brochure.
Automated Scissors Drive, Medical Products, Catalog.
Oscillating Knife, Grieshaber & Co. Inc.
Dorc Instrumention For Use With Micro Surgical Systems for Anterior and Posterior Segment Surgery, Catalog.
High–Technology Accessories Low–Cost Disposability, Alcon Vitreoretinal 1991.
Glaucoma Mechanical Trephine, Trek, Medical Products.

*Primary Examiner*—Michael Buiz
*Assistant Examiner*—Julian W. Woo
*Attorney, Agent, or Firm*—Grant D. Kang

[57] ABSTRACT

A system for controlling a plurality of ophthalmic microsurgical instruments is disclosed. Particularly, the present invention includes a handpiece for activating a surgical instrument (i.e., such as scissors) connected to the handpiece. The handpiece includes a housing and a linear activator operatively retained within the housing. A nosepiece is mounted to one end of the housing and is adapted for correction of a linearly actuated surgical instrument. The nosepiece is fixed to the linear activator in a preselected calibrated position relative to the longitudinal axis of the linear actuator.

2 Claims, 3 Drawing Sheets

U.S. PATENT DOCUMENTS

| | | | |
|---|---|---|---|
| 4,757,814 | 7/1988 | Wang et al. | 128/318 |
| 4,760,848 | 8/1988 | Hasson | 128/340 |
| 4,768,506 | 9/1988 | Parker et al. | 128/303 |
| 4,786,022 | 11/1988 | Grieshaber | 248/287 |
| 4,813,401 | 3/1989 | Grieshaber | 128/20 |
| 4,877,026 | 10/1989 | de Laforcade | 128/305 |
| 4,898,575 | 2/1990 | Fischell et al. | 604/22 |
| 4,911,161 | 3/1990 | Schechter | 606/171 |
| 4,938,214 | 7/1990 | Specht et al. | 128/340 |
| 4,947,871 | 8/1990 | Grieshaber | 128/898 |
| 4,986,825 | 1/1991 | Bays et al. | 604/22 |
| 5,020,535 | 6/1991 | Parker et al. | 606/174 |
| 5,024,652 | 6/1991 | Dumenek et al. | 604/22 |
| 5,047,008 | 9/1991 | de Juan, Jr. et al. | 604/22 |
| 5,085,662 | 2/1992 | Willard | 606/159 |
| 5,087,265 | 2/1992 | Summers | 606/159 |
| 5,094,260 | 3/1992 | Stuart et al. | 137/102 |
| 5,123,904 | 6/1992 | Shimomura et al. | 604/22 |
| 5,176,628 | 1/1993 | Charles et al. | 604/22 |
| 5,263,958 | 11/1993 | deGuillebon et al. | 606/174 |
| 5,273,530 | 12/1993 | del Cerro et al. | 604/51 |
| 5,275,607 | 1/1994 | Lo et al. | 606/169 |
| 5,284,472 | 2/1994 | Sussman et al. | 604/22 |
| 5,314,440 | 5/1994 | Shapiro | 606/174 |
| 5,355,871 | 10/1994 | Hurley et al. | 128/20 |
| 5,360,398 | 11/1994 | Grieshaber et al. | 604/30 |
| 5,370,658 | 12/1994 | Scheller et al. | 606/205 |
| 5,409,457 | 4/1995 | del Cerro et al. | 604/51 |
| 5,443,473 | 8/1995 | Miller et al. | 606/166 |
| 5,443,476 | 8/1995 | Shapiro | 606/174 |
| 5,454,783 | 10/1995 | Grieshaber et al. | 606/30 |
| 5,474,532 | 12/1995 | Steppe | 604/22 |
| 5,487,747 | 1/1996 | Staqgmann et al. | 606/166 |

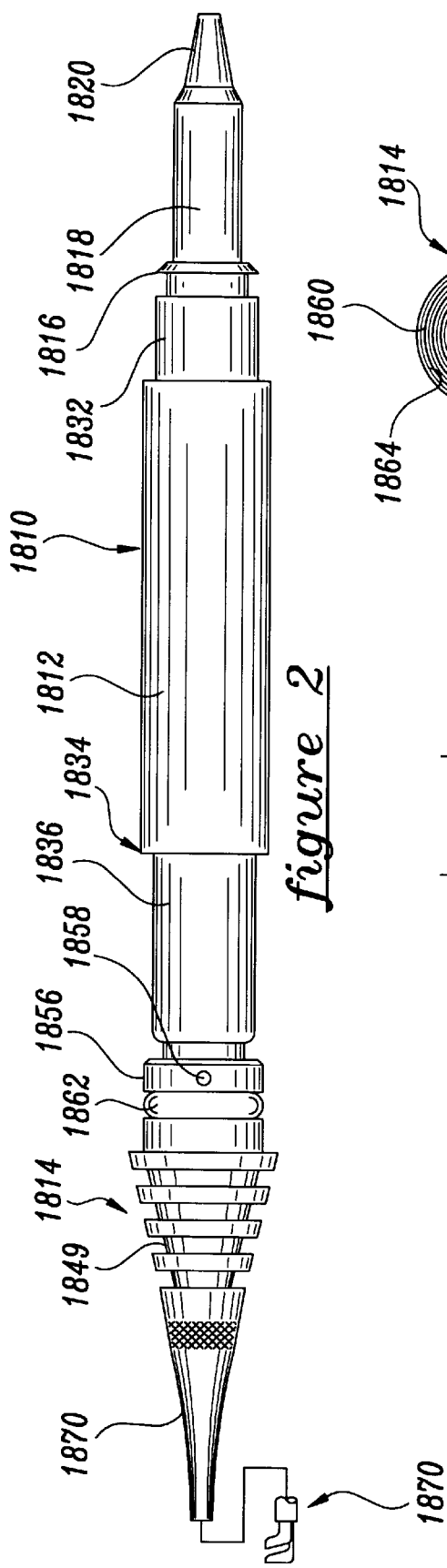
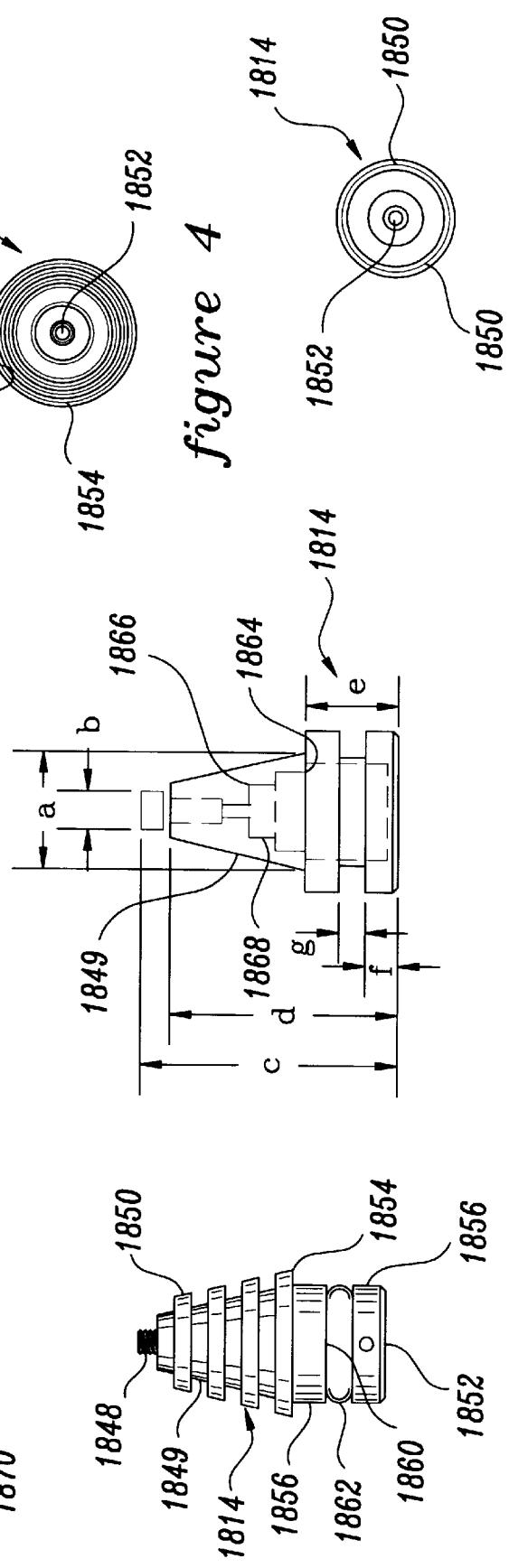
figure 2
figure 4
figure 5
figure 5A
figure 3

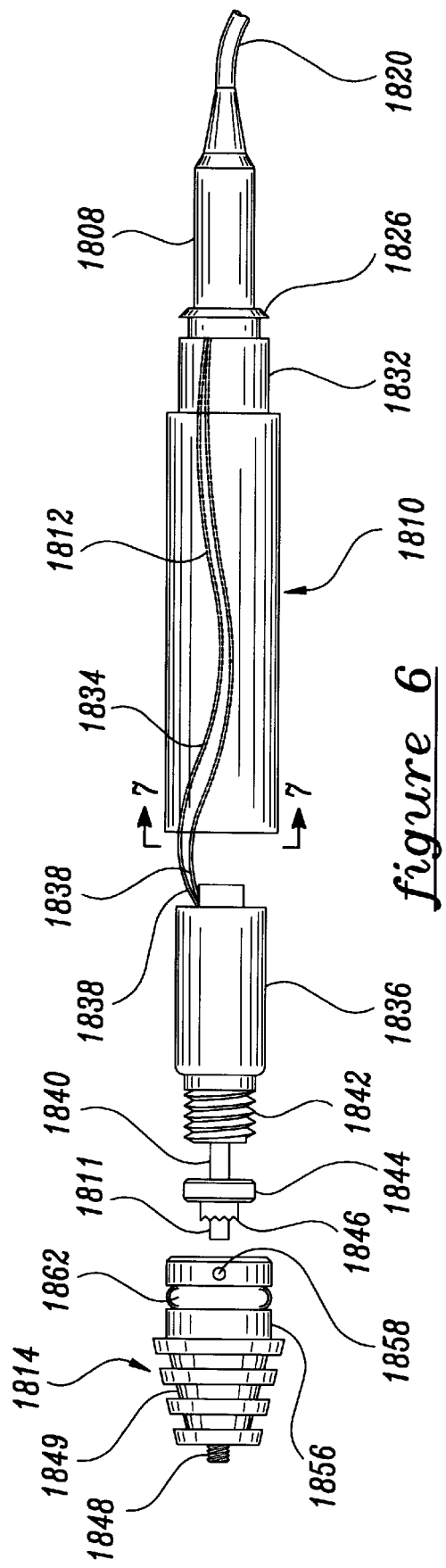
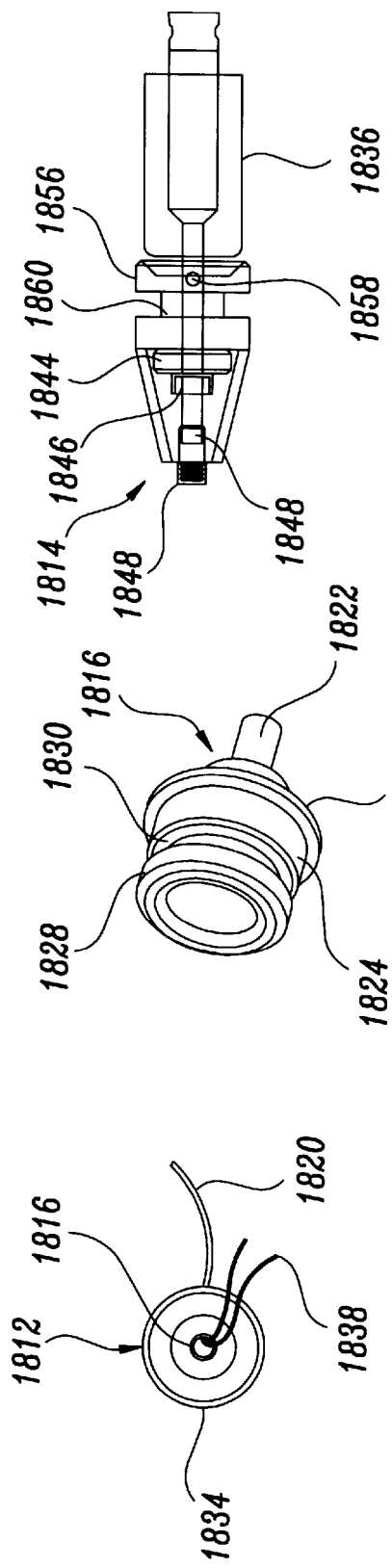
figure 6
figure 7
figure 8
figure 9

SURGICAL HANDPIECE

MICROFICHE APPENDIX

This application includes a microfiche appendix which is a copy of the provisional application under which priority is claimed.

BACKGROUND OF THE INVENTION

This invention relates generally to microsurgical and ophthalmic systems and, particularly, to a control system which utilized various surgical instruments to a handpiece intended for ophthalmic surgical scissors of the "vertical" type, which handpiece can be activated by a foot pedal controlled linear solenoid motor and such handpiece's method of manufacture.

Present day ophthalmic microsurgical systems provide one or more surgical instruments connected to a control console. The instruments are often electrically or pneumatically operated and the control console provides electrical or fluid pressure control signals for operating the instruments. The control console usually includes several different types of human actuable controllers for generating the control signals supplied to the surgical instruments. Often, the surgeon uses a foot pedal controller to remotely control the surgical instruments.

The use of intraocular surgical scissors is well known. While manually operated scissors are still in widespread use worldwide, they suffer from the disadvantage of being subject to human limitations on speed and accuracy. The use of surgical scissors with electric motor drive is also widespread. Electrical motor driven scissors are divided into two well known types based upon the type of drive, those that are solenoid actuated and those that are driven by a direct current motor or "proportional" control.

Most intraocular scissors have design similarities in which a pair of cutting blades extend from the end of a tubular "needle", with one blade being fixed and the other, opposed blade end being reciprocated between an open and a closed position with respect to the fixed blade. This reciprocating motion is accomplished through the action of one of the driving systems mentioned, such as, for example, a manual or electric motor drive.

Electric motor drivers of either rotary or linear solenoid type activate scissor closure by controlled transfer of the motor energy to the movable blade. The scissors may be of the "vertical" design (the guillotine, or the parallel blade type), the angled or "horizontal" style, or of another design, or the driver may instead be used to actuate other instruments, besides scissors, that operate similarly.

The linear solenoid type of drive provides a reciprocating action in which the electrical actuation of a solenoid causes the movable blade to move to the closed position in relation to the fixed blade and then, usually through the operation of a spring within the hub of the scissors, to return to the open position. An example of a handpiece of this type is seen in the patent which issued to Lo et al., U.S. Pat. No. 5,275,607.

It is characteristic of solenoid actuated scissors handpieces that the cutting action provided be a rapid, snipping action, due to the fast firing of the solenoid plunger or piston. Thus, the solenoid actuated style of handpiece is appropriate for use with a surgical scissor of the known guillotine type, such as (as one example only) the scissor tip presently offered by STORZ® Ophthalmic Instruments Co. under the trademark ERGOTEC as product number E8700.

By contrast, when a more controlled instrument action is required, for example, for careful cutting or pinching, the proportional-type of motor and the incremental movement provided thereby is generally preferred. Thus, the proportional type of motor control, such as is provided by a stepper motor is appropriate for use when the operating instrument is a forceps or a conventional "horizontal" style of ophthalmic scissors or other instrument (e.g. ERGOTEC tip E8500 or E8600). Thus, the new handpiece described herein for use with a solenoid motor is capable of using a known type of surgical instrument tip, without the necessity of alteration or adaptation of the instrument.

An example of a known proportional control/handpiece is seen in U.S. Pat. No. 4,757,814, which issued to Wang et al., for a pneumatic cutting device. However, that device, although disclosed as proportional, includes a linear solenoid valve actuated by a selectively varied electrical signal generated by a power supply and controlled by a potentiometer which is in turn operated by a foot pedal.

One difficulty which occurs in manufacture of linear solenoid actuated handpieces for surgical instruments is related to the inconsistencies in product dimensions which necessarily occur during manufacture of parts. The differences of particular concern here are those that occur among solenoid piston lengths and between the lengths of actuating pins in surgical instruments of the type which are used in ophthalmic surgery. Variations between individual parts can cause even a new instrument to be non-functional, or to wear or operate improperly and break down prematurely, because the actuator pin is not met be the drive piston or because the actuator pin is driven too far.

SUMMARY OF THE INVENTION

Accordingly, the solenoid actuated handpiece described herein, including the unique nosepiece element of the handpiece, and the method of assembling the new handpiece directly address the problem of variations in dimensions of machined parts and provide an improved solenoid actuated handpiece for ophthalmic surgical instruments, which handpiece has increased reliability of operation and durability.

Of course, although intended especially for use with ophthalmic instruments, the new handpiece construction may also be well suited for other types of electrically operated surgical instruments. Thus, although described with relation to a vertical ophthalmic scissors, it is not intended that the new handpiece and the nosepiece thereof be so limited in use.

Moreover, although the nosepiece element is described herein specifically in relation to the new handpiece as a whole, it is certainly conceivable that the nosepiece could be used, when constructed exactly as described or with reasonable and appropriate modifications, with other styles of handpieces, potentially even a manually operated style of handpiece. In other words, as long as the nosepiece can be connected to a linear actuator in a preselected position and also be capable of operable connection to a surgical instrument, it is considered to be within the scope of the invention.

It is among the advantages of the present invention that the new handpiece be simple in construction relative to known devices and that it thus be relatively facile and economical to manufacture. Moreover, the new handpiece is intended to be controlled by a foot pedal connected to a new modular electronic control unit, as described elsewhere herein.

Accordingly, in furtherance of the above goals and advantages of the new device and method of manufacture, the invention is, briefly, a handpiece for actuating a surgical instrument connected to the handpiece. The new handpiece includes a housing and a linear actuator operatively retained within the housing. A nosepiece is mounted to one end of the housing and is adapted for connection of a linearly actuated surgical instrument. The nosepiece is fixed to the linear actuator in a preselected calibrated position relative to the longitudinal axis of the linear actuator and the other end of the housing is enclosed and liquid-tight.

The invention is also, briefly, a nosepiece for connecting a surgical instrument to a linear actuator in a preselected position relative to a longitudinal axis of the linear actuator. The nosepiece is mountable to the linear actuator and includes structure for detachable connection of the nosepiece to a surgical instrument, and structure for adjustably mounting the nosepiece to the linear actuator and for fixing the nosepiece to the linear actuator in a preselected position.

The invention is still further, briefly, a method of manufacturing a handpiece for surgical instruments actuated by a linear actuator. The method includes constructing a nosepiece assembly for the handpiece by a) placing a slide fit seal and a press fit washer into a nosepiece, b) adjustably introducing a forwardly directed end of a linear actuator into the nosepiece, c) inserting a plunger of the linear actuator into a rearwardly directed end of the nosepiece, d) holding the plunger of the linear actuator in the inserted position in the nosepiece, e) calibrating the longitudinal position of the linear actuator relative to the nosepiece, which longitudinal position is required to achieve operative contact of the plunger of the linear actuator with an actuator pin of a surgical instrument which is connectable to the nosepiece, and f) fixing the longitudinal position of the linear actuator at the calibrated setting.

These and other goals and advantages of the invention will be in part apparent and in part pointed out hereinbelow.

BRIEF DESCRIPTION OF THE DRAWINGS

FIG. 2 is a side elevation of a scissors handpiece embodying the present invention, nearly fully assembled;

FIG. 3 is a side elevation of a nosepiece of the handpiece of FIG. 2;

FIG. 4 is a top plan of the nosepiece of FIG. 3;

FIG. 5 is a bottom plan of the nosepiece of FIG. 3;

FIG. 5A is a schematic side elevation of the nosepiece of the handpiece of FIG. 2, enlarged for clarity and showing the internal contours in phantom;

FIG. 6 is an exploded side elevation of the handpiece of FIG. 2 with the scissors removed for clarity;

FIG. 7 is an elevation taken on line 7—7 of FIG. 6, showing the internal aspects of the handpiece and power cord interconnection, with the wiring moved aside, for clarity;

FIG. 8 is a perspective of a tailpiece of the handpiece of FIG. 2, enlarged for clarity;

FIG. 9 is a schematic side view of the nosepiece and a solenoid assembly of the handpiece of FIG. 2, enlarged for clarity and showing the position of the unactuated solenoid piston in phantom.

DETAILED DESCRIPTION OF INVENTION

Figure 1:
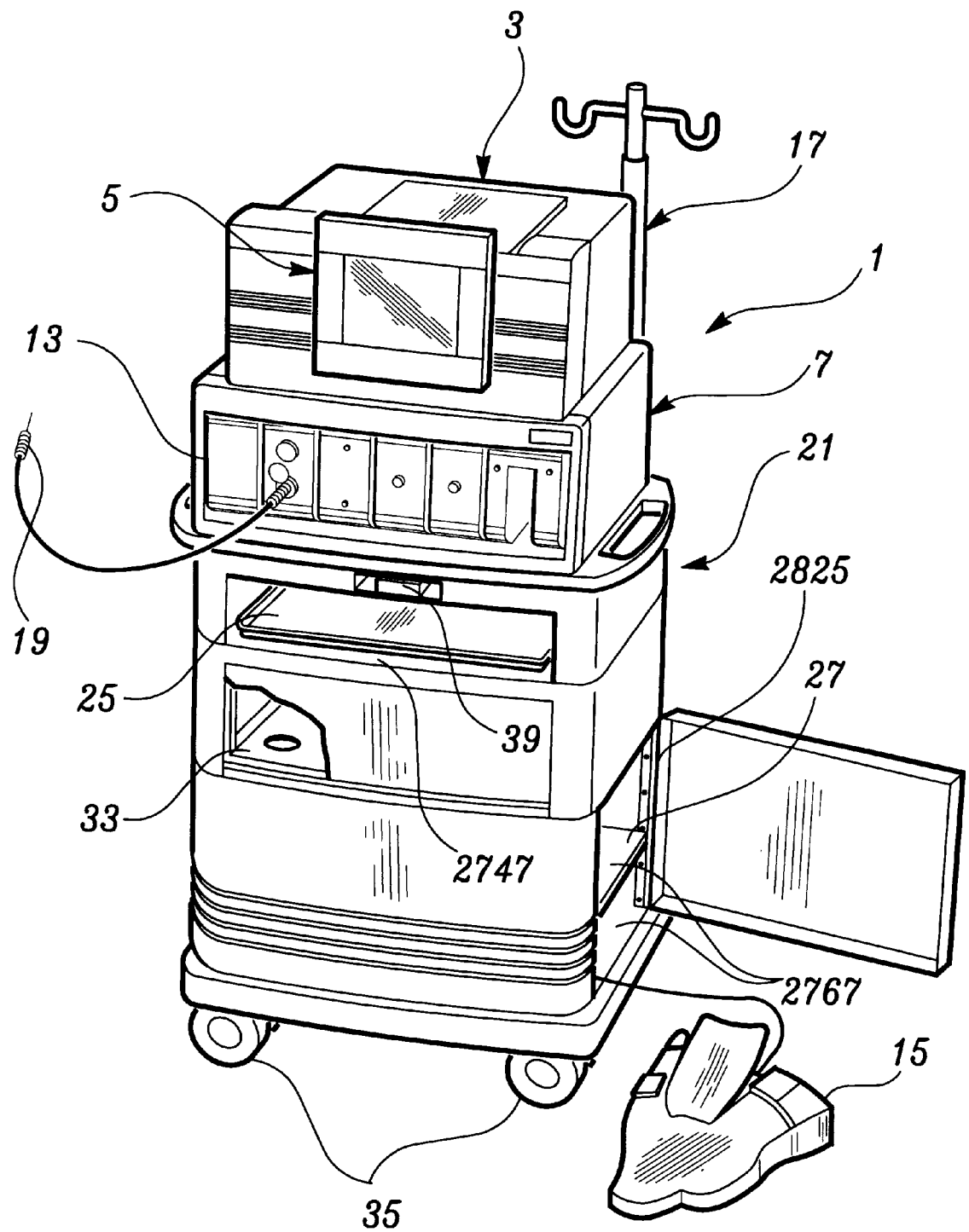
FIG. 1 is a perspective view of a microsurgical control system for use with ophthalmic microsurgical instruments, and having a plurality of control modules utilizing a variety of surgical handpieces in accordance with the present invention.

Referring to the accompanying drawings in which like reference numbers indicate like elements, FIG. 1 illustrates a microsurgical control system, generally designated 1, according to a preferred embodiment of the present invention. As shown, the system 1 includes a computer unit 3 having a flat panel display 5, a base unit 7 housing a plurality of modules 13, and peripherals such as a foot control assembly 15 and a motorized intravenous (IV) pole assembly 17 (each of which is generally indicated by its respective reference numeral). Each of the modules 13 housed in the base unit 7 controls at least one ophthalmic microsurgical instrument 19 for use by a surgeon in performing various ophthalmic surgical procedures.

As is well known in the art, ophthalmic microsurgery involves the use of a number of different instruments 19 for performing different functions. These instruments 19 include vitrectomy cutters, phacoemulsification or phacofragmentation handpieces, electric microscissors, fiber optic illumination instruments, coagulation handpieces and other microsurgical instruments known in the art. To optimize performance of instruments 19 during surgery, their operating parameters differ according to, for example, the particular procedure being performed, the different stages of the procedure, the surgeon's personal preferences, whether the procedure is being performed in the anterior or posterior portion of the patient's eye, and so on.

As shown in FIG. 1, an instrumentation cart, generally designated 21, supports system 1. Preferably, the cart 21 includes a surgical, or Mayo, tray 25, the automated IV pole assembly 17, a storage compartment 27 for stowing the foot control assembly 15, disposable packs and other items, an opening 33 to house an expansion base unit (not shown in FIG. 1), and rotating casters 35. Base unit 7 and computer unit 3 preferably sit on top of instrumentation cart 21 as shown in FIG. 1 and the Mayo tray 25 is mounted on an articulating arm (not shown) preferably attached to the top of instrumentation cart 21, directly beneath base unit 7. Instrumentation cart 21 also holds a remote control transmitter, generally indicated 39, for use in remotely controlling system 1.

The modules 13 in base unit 7 house control circuits for the various microsurgical instruments 19 so that the system's user is able to configure system 1 for optimizing its use by the surgeon. Modules 13 include connections or ports by which one or more microsurgical instruments 19 connect to each module 13 and house the necessary control circuitry for controlling operation of the particular instrument or instruments 19 connected thereto. Thus, the user, by inserting the desired modules 13 in base unit 7, configures system 1 to meet a particular surgeon's preference, to control each of the instruments 19 needed for a particular surgical procedure, or to otherwise optimize system 1 for use by the surgeon.

Referring now to FIGS. 2–9 of the drawings, and initially with reference to FIGS. 2 and 6, 1810 generally designates a handpiece constructed in accordance with and embodying the present invention. Preferably, the handpiece 1810 is for use with a module 13 and, particularly, with a scissors module 3, more fully described in copending application which is hereby incorporated by reference. Handpiece 1810 is, in basic terms, composed of a central housing 1812 having a nosepiece 1814 connected at the forward or working end of housing 1812 and a tailpiece 1816 connected at the opposed, rearwardly directed end of housing 1812. Throughout this description the term "forward" refers to the end of handpiece 1810 to which a surgical instrument is operatively connected, and "rearward" refers to the end of the handpiece attached by a power cable 1820 to a control device.

Housing 1812 is preferably elongated and cylindrical as shown, but could of course take other general forms, as long as the structure is suitably conformed to be held by hand (or conceivably, and alternatively, by a robotic grasping device which functions as a surgeon's hand) and to receive and retain a linear, solenoid motor and connect to (preferably by press-fit construction) the tailpiece 1816 and nosepiece 1814, to be described.

Tailpiece 1816 is preferably a single piece and formed of stainless steel. However, other materials and constructions exist or can be conceived which will suffice. ordinarily the tailpiece is circular in cross-section to properly engage and seal the rearwardly directed end of housing 1812. However, should the cross-sectional shape of the housing be altered, a corresponding change can be incorporated into the tailpiece to ensure a secure, liquid-tight fit between the two pieces.

Shown enlarged in FIG. 8 in its preferred form, tailpiece 1816 has a tubular extension 1822 to which is connected a cable strain relief 1818 (shown in FIGS. 2 and 6) which extends rearwardly and receives and protects a conventional power cable 1820 (which is connected to the control module 13 previously mentioned) from strains and stresses caused by twisting, pulling and bending in the normal course of use of handpiece 1810. Cable relief 1818 is desirably formed of silicone or some other suitably pliable substance which is strong, yet somewhat flexible and is preferably molded to extension 1822 or otherwise applied thereover as a sleeve and which is easy to clean.

Tubular extension 1822 of tailpiece 1816 intersects and is contiguous with an intermediate section 1824 which is provided on the forwardly directed end thereof with a flange 1826 which abuts the rearwardly directly annular open end of housing 1812. Extending forwardly from flange 1826 is a cylindrical insertion section 1828 which is of sufficient size to press fit into the rearwardly directed end 1832 of housing 1812.

The insertion section 1828 of tailpiece 1816 is provided with an annular groove 1830 which serves as a seat for a conventional O-ring (not shown), to thereby further ensure a liquid-tight seal with the inside wall of rearwardly directed end of housing 1812. Certainly other structures are suitable for tailpiece 1818 which will acceptably serve the purposes of enclosing the tail end (power cord end) of housing 1812 while simultaneously providing strain relief for power cable 1820.

The rearwardly directed end 1832 of housing 1812 is illustrated as being somewhat tapered, axially inwardly, relative to the main body of the housing. Although this design is preferred, other forms are suitable for this area of device 1810 that will not substantially affect the function of the device.

Also, it is preferred that housing 1812 be formed of stainless steel, but of course other materials both existing and possibly to be developed will suffice if the material is strong, durable and capable of being repeatedly disinfected as may be necessary after the medical procedure for which handpiece 1810 is used. If desired, housing 1812 may be provided with a coating, for example of an elastomer, applied by molding or otherwise, to improve user comfort.

Although, as discussed above, it is intended that handpiece 1810 be connected to a power source by a conventional power cable 1820, it is conceivable that handpiece 1810 could alternatively, or additionally, be provided with a battery as a source of power. For example, a battery of appropriate size and power could be disposed within the rearwardly directed end of housing 1812 and a control switch could be incorporated into handpiece 1810 or in connection therewith so that the surgeon could operate handpiece 1810, for example, in remote locations, without requiring the entire modular control unit previously discussed as the preferred form of the invention.

FIGS. 2, 6 and 7 illustrate that the forwardly directed end 1834 of housing 1812 longitudinally receives a known linear solenoid 1836, which is connected by lead wires 1838 to power cable 1820 in the usual manner. One example of a suitable solenoid presently available is marketed by the Lucas Company and referred to as an STA Series Push type. The solenoid carrying part number 195203-331 is particularly appropriate and is approximately one inch long and about one half inch wide, with a plunger that is approximately one and seven eighths inch long.

Certainly other push type solenoids will also suffice provided that they have suitable specifications for the functions described herein. For example, if a smaller diameter handpiece is preferred, a smaller solenoid is necessary in order that it operably fit into the housing.

A plunger or piston 1840 is slideably disposed longitudinally within solenoid 1836 so as to be actuated forwardly when the solenoid is signaled via the previously mentioned foot control 15. The forwardly directed end of solenoid 1836 is provided with male external threads 1842 for adjustable connection to nosepiece 1814, which will be described hereafter. In the preferred design, using the STA style solenoid discussed elsewhere herein, the male thread on end 1842 is ⅜–24, although this specification can vary if a different size handpiece housing and solenoid are used.

As shown in FIGS. 6 and 9, coaxially mounted on solenoid piston 1840 are a press fit washer 1844 and a slide fit seal 1846, disposed forwardly of washer 1844, which serves to retain seal 1846 within nosepiece 1814. It is preferred (although not necessarily required) that slide fit seal 1846 be of a particular known and commercially available variety which is formed of TEFLON® or other similar moldable slick substance, and which is provided with an internal coil spring which biases seal 1846 radially outwardly and inwardly as the solenoid piston 1840 travels forwardly and rearwardly coaxially through both washer 1844 and seal 1846 within nosepiece 1814.

Nosepiece 1814 is illustrated in FIGS. 2, 3, 5A and 6 as having a shape substantially that of a truncated cone with a male threaded forwardmost tip 1848. Threaded end 1848 is suitably formed to selectively removably engage in the usual manner the female threaded hub 1870' of a guillotine type ophthalmic scissor, such as that previously mentioned and as illustrated, for example only, in FIG. 2 at 1870. Thus, the male thread provided on end 1848 is preferably #10–32.

Various manufacturers produce similar scissors which can have a different thread or other connection structure than the ERGOTEC™ device previously mentioned. In that case, the nosepiece tip 1848 can be altered as necessary, in known manner, to operatively connect to the surgical instrument hub.

Nosepiece 1814 has a gripping end 1849 with a smooth, sloped outer surface, tapering forwardly to tip 1848, for example of polished stainless steel with which the entire nosepiece 1814 is preferred to be formed. Alternatively, the forwardly angled gripping portion 1849 can be coated, at least in part, with some other substance, such as silicone or an elastomer in such manner that the surface is still smooth, or molded so as to have ridges, such as those indicated at 1850 in FIGS. 3 and 5, as one example only, in order to provide an improved grip, both for comfort and to reduce the risk of an attached surgical instrument slipping in the surgeon's hand.

FIGS. 4 and 5 illustrate a central longitudinal aperture 1852 within nosepiece 1814 through which the actuator pin (not shown) of scissors 1870 is contacted endwise by the forwardly directed, tip 1841 of solenoid piston 1840, when piston 1840 is in the actuated position shown in solid lines in FIG. 9. The broken lines in FIG. 9 illustrate the position of piston 1840 in a de-energized, retracted state to which the piston returns after actuating the surgical instrument. Ordinarily return to this position (indicated at 1843 in FIG. 9) is caused, at least in part, by a known spring mechanism within hub 1870.

The rearwardly directed end of nosepiece 1814 consists of an annular flat surface 1854, illustrated in FIG. 4, which faces the forwardly directed end of solenoid 1836. Internally of end face 1854, nosepiece 1814 has a straight, cylindrical wall which is sized and female-threaded to receive to corresponding male-threaded end 1842 of solenoid 1836. Externally, end face 1854 extends radially outwardly until intersecting a straight annular outer side wall 1856. Like other edges of the nosepiece, the edge of the intersection between end face 1854 and side wall 1856 may be chamfered, as shown, if desired for comfort and convenience of use.

Outer side wall 1856 is provided with preferably at least three (equally spaced apart), but necessarily at least one, transverse, internally threaded hole 1858 for receiving known set screws (e.g. #2–56 screws, not shown) in the usual manner to thereby attach threaded end 1842 of solenoid 1836 in a preselected position longitudinally within nosepiece 1814, as will be described further hereafter.

Outer side wall 1856 is desirably provided with a formed annular groove 1860 for receiving a conventional O-ring 1862 so that nosepiece 1814 fits tightly against the cylindrical inner side wall of housing 1812. Annular groove 1860 is seen most clearly in FIG. 9, where the O-ring is omitted. O-ring 1862 is shown in FIG. 2, and in section in FIGS. 3 and 6.

Continuing forwardly within nosepiece 1814 from the threaded inner wall of the rearwardly directed end, i.e., the view seen in FIG. 4, there are formed a pair of ledges or shoulders, shown most clearly in the schematic FIGS. 5A and 9, and indicated at 1864 and 1866. A straight sided annular wall 1868 extends between shoulders 1864 and 1866 and provides a circumferential boundary for slide fit seal 1846 as the solenoid piston 1840 travels longitudinally during actuation and return. Wall 1868 terminates forwardly in inwardly directed annular shoulder 1866 and forms an outward boundary for slide fit seal 1846. Press fit washer 1844 which seats against shoulder 1864 rearwardly of seal 1846 and is press fit against the inside wall of the nosepiece. As such, the slide-fit seal is retained in a preselected position within the nosepiece and the motor shaft can move longitudinally coaxially within both the slide fit seal and the press fit washer positioned behind the seal.

Overall, handpiece 1810 is formed of materials which are durable and amenable to being repeatedly cleaned and disinfected without readily breaking down. Further, as discussed, the general form of handpiece 1810 can be varied somewhat and still function adequately. It is necessary, however, that the solenoid piston be positioned in axial alignment with the tip of the actuating pin of the scissors. For the preferred assembly, of course, the nosepiece described herein, or its functional equivalent is necessary.

With reference to FIG. 5A, the following dimensions for the distances indicated in the figure by arrows a–g are provided as an example of nosepiece 1814 constructed within the scope of the invention. It is to be understood that the figures provided are not intended to be limiting, but only exemplify a preferred form of nosepiece 1814. In thousands of an inch, the preferred dimensions for nosepiece 1814 are: a—0.450, b—0.240, c—1.031, d—0.906, e—0.406, f—0.146, and g—0.094/0.104.

During manufacture, the sequence of steps to assemble the nosepiece assembly (i.e. the nosepiece, solenoid and solenoid plunger with slide fit seal and press fit washer) of handpiece 1810 is as follows: 1) slide fit seal 1846 and press fit washer or bushing 1844 are installed into nosepiece 1814, 2) threaded end 1842 of solenoid 1836 is screwed onto nosepiece 1814, 3) solenoid plunger 1840 is inserted into solenoid 1836, forwardly toward nosepiece 1814, 4) while holding solenoid plunger 1840 in the previously mentioned seated position within solenoid 1836, nosepiece 1814 is rotated to achieve a previously determined gauge setting (or a calibration value with a dial indicator); i.e., tip 1841 of plunger 1840 is positioned longitudinally relative to nosepiece 1814 for proper functioning of scissors 1870, and 5) the set screws are installed transversely into nosepiece 1814 and tightened against threaded end 1842 of solenoid 1836 to secure nosepiece 1814 to solenoid 1836 in the preselected longitudinal position.

After the above steps have been performed the assembled nosepiece assembly is press fit into forwardly directed end 1834 of housing 1812 and tailpiece 1816 is press fit into rearwardly directed end 1832 of housing 1812.

So assembled, handpiece 1810 is preset so that no adjustment or additional assembly is required by the surgeon. Rather, the user should not attempt to disassemble the handpiece, as doing so would more than likely disrupt the carefully calibrated positioning of the solenoid plunger relative to the tip of the nosepiece, i.e., relative to the actuated needle tip of the surgical instrument detachably connected to the nosepiece.

Thus, it can be readily seen that the overall structure and method of assembly of the new handpiece 1810 is greatly simplified relative to known handpieces, and the new handpiece is therefore more economical to manufacture and is facile to use, without any additional, specialized training beyond that already possessed by the surgeon.

In view of the foregoing, it will be seen that the several objects of the invention are achieved and other advantages are attained.

Although the foregoing includes a description of the best mode contemplated for carrying out the invention, various modifications are contemplated.

As various modifications could be made in the constructions herein described and illustrated without departing from the scope of the invention, it is intended that all matter contained in the foregoing description or shown in the accompanying drawings shall be interpreted as illustrative rather than limiting.

I claim:

1. A handpiece for actuating a linearly actuated surgical instrument connected to the handpiece comprising:
   a linear actuator operatively retained within the housing having a longitudinal, distal tip;
   a nosepiece mounted to the first end of the housing and adapted for connection of a surgical instrument, the nosepiece being fixed to the linear actuator in a preselected calibrated position relative to the longitudinal tip of the linear actuator; and
   the second end of the housing being enclosed and liquid-tight, wherein the nosepiece is provided at least in part with a slick coating.

2. A handpiece for actuating a linearly actuated surgical instrument connected to the handpiece comprising:
- a linear actuator operatively retained within the housing having a longitudinal, distal tip;
- a nosepiece mounted to the first end of the housing and adapted for connection of a surgical instrument, the nosepiece being fixed to the linear actuator in a preselected calibrated position relative to the longitudinal tip of the linear actuator; and
- the second end of the housing being enclosed and liquid-tight, wherein the nosepiece has an elastomeric soft-grip coating.

* * * * *